United States Patent [19]

Singh et al.

[11] 3,953,444

[45] Apr. 27, 1976

[54] CYCLIC AND POLYCYCLIC DIAZADIOXIDES AS QUENCHERS AND RADICAL INHIBITORS

[75] Inventors: Prithipal Singh, Sunnyvale; Edwin F. Ullman, Atherton, both of Calif.

[73] Assignee: Syva Company, Palo Alto, Calif.

[22] Filed: May 9, 1973

[21] Appl. No.: 358,758

Related U.S. Application Data

[63] Continuation-in-part of Ser. No. 196,724, Nov. 8, 1971, abandoned.

[52] U.S. Cl. .................... 260/250 AC; 260/239 A; 260/250 A; 260/666 C; 260/666.5; 260/45.8 NZ

[51] Int. Cl.² ........................................ C07D 237/26

[58] Field of Search ............................. 260/250 AC

*Primary Examiner*—Richard J. Gallagher
*Assistant Examiner*—D. B. Springer
*Attorney, Agent, or Firm*—Townsend and Townsend

[57] ABSTRACT

Heterocyclic diazadioxides, having the two nitrogen atoms as annular atoms, are employed as quenchers for molecules in the excited state. The compounds can be used in combination with polymers and pigments for protection against light and oxidative attack. The products are also found to be efficient free radical inhibitors. Heterocyclic mono- and polycyclic diazadioxides are provided. All of the compounds are found to have relatively low triplet energy values.

3 Claims, No Drawings

CYCLIC AND POLYCYCLIC DIAZADIOXIDES AS QUENCHERS AND RADICAL INHIBITORS

CROSS-REFERENCE TO RELATED APPLICATIONS

This application is a continuation in part of application Ser. No. 196,724, filed Nov. 8, 1971, now abandoned.

BACKGROUND OF THE INVENTION

1. Field of the Invention

In photochemical reactions, the course of the reaction can be affected by the excited state from which the product is formed. The excited state is determined initially by the energy absorbed by the molecule, but the initial state may be changed by interaction with the molecule's environment. Singlet and triplet states are the common photochemical excited states, which may be achieved by either direct absorption of energy, particularly light, or by use of a sensitizer.

The reaction product can depend on the excited state from which the reaction product is derived, not only as to isomer, but also in some cases as to structure, such as cyclizations. Therefore, where the possibility exists for two different products to be obtained, depending on the nature of the excited state, a quencher may be employed to dissipate the energy of one of the excited states in a manner which does not result in product formation.

Quenchers also find use in the study of photochemical reactions. In order to ascertain whether a particular product is formed through a triplet or singlet state, a quencher may be employed which will prevent the reaction from going through a triplet state. In this manner, if the reaction proceeds in the presence of the quencher, assuming the quencher has the appropriate triplet energy value ($E_T$), then the triplet state of the reactant must be very short lived or the reaction must proceed by means of a singlet state.

The lower the triplet energy value for a molecule which is undergoing reaction, the lower the triplet energy value required for the quencher. Therefore, quenchers with low triplet energy values can be quite valuable in being able to quench reactions which occur at relatively low energy values. However, the quencher must not absorb the exciting light as this would inhibit the photochemical reaction. Ideal quenchers, therefore, have high singlet energies, preferably greater than about 60 kcal/mode, and low triplet energies, preferably less than about 45 kcal/mole.

In addition, numerous degradative reactions of both dyes and polymeric materials are the result of free radical reactions. A free radical is usually formed initially, which can react with oxygen to form a peroxide or hydroperoxide. Breakage of the oxygen-oxygen bond results in the formation of additional radicals which, by abstraction or addition, form new radicals, which then add to oxygen. Since cleavage of the peroxide gives two radicals, the process is autocatalytic. By providing a material which is stable but reactive toward radicals, the chain of peroxide formation can be broken and the life of the host or substrate material greatly extended.

2. Description of the Prior Art

A list of quenchers may be found in the 1971 J. T. Baker catalog. A description of the use of quenchers may be found in Turro, "Molecular Photochemistry", Benjamin, New York, 1967. The reaction of 1,2-bis(-hydroxylamino)tetramethylethane is reported to give a 1-oxylaziridine in Luckhurst, et al, Tetrahedron Letters, 1971, 675. Heterocycles having the diazoxy functionality are reported by Snyder, et al, Tetrahedron Letters, 1971, 4693; Tun, et al, Org. Mass. Spect. 3, 1055 (1970) Luttke, et al, Liebigs, Ann. Chem 687, 236 (1965), Beilstein II, Band V. pg. 26 (Piloty, et al, Ber. 35, 1303) particularly 1,4 dibromo, and 1,4 dichloro-2,3-diazabicyclo[2,2,2]oct-2 en-2,3-dioxide and 2,3-diazabicyclo[2,2,1]hept-2-en-2,3-dioxide.

SUMMARY OF THE INVENTION

Heterocyclic diazadioxides are employed for quenching excited states of molecules, particularly molecules in the excited triplet state, preventing formation of singlet state oxygen, as well as finding use as free radical inhibitors, particularly with pigments and polymeric materials which are subject to light or oxidative change or degradation. Novel cyclic diazadioxides are provided including both mono- and polycyclic (caged) compounds.

DESCRIPTION OF THE SPECIFIC EMBODIMENTS

N,N'-dioxide diazacycloalkenes (diazoxycycloalkenes), both mono- and polycyclic, are employed with substrates, either liquid or solid, to provide triplet quenching and/or anti-oxidant activity for media susceptible to light induced oxidation, and free radical formation, particularly material susceptible to free radical formation and addition of oxygen to form peroxides with subsequent change in the physical or chemical properties of the material. The compounds employed in this invention find particular use with pigments to inhibit fading, and with polymeric materials, subject to oxidation attack, either light and/or free radical initiated.

The compounds employed in this invention may be either mono- or polycyclic having two or more fused rings, usually not more than hexacyclic, more usually, not more than pentacyclic. The compounds will normally be from about six to thirty-six carbon atoms, more usually from about six to twenty-four carbon atoms and for the most part, about six to sixteen carbon atoms. The compounds will usually have the two nitrogen atoms of the diazadioxide as the only heteroannular members.

Each of the nitrogen atoms will be bonded to a carbon atom which is either bonded to other than hydrogen, usually carbon or halogen, or bonded to a hydrogen atom at a bridge head of a bicyclic ring. The remaining valences of the carbon atom bonded to the nitrogen atoms may be satisfied by bonding to each other, or bonding to hydrocarbon groups which are either mono-valent or poly-valent, so as to form additional rings. The number of annular atoms other than nitrogen may vary from two to 18, more usually to 14.

For the most part, the compounds of this invention will have the following formula:

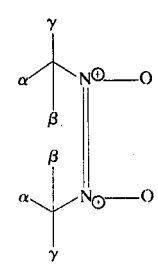

wherein at least one of the pairs of alphas and betas form a bond or a divalent radical of from 1 to 16 carbon atoms, more usually of from 1 to 12 carbon atoms, or the pair of alphas and the pair of betas may be taken together to form a tetravalent radical of from 3 to 16 carbon atoms, more usually of from 4 to 12 carbon atoms; more particularly, the two alphas may be the same or different and may be hydrocarbon or substituted hydrocarbon of from 1 to 12 carbon atoms, more usually aliphatic (free of aromatic unsaturation) hydrocarbon; substituted hydrocarbon having from 0 to 1 site of ethylenic unsaturation and preferably aliphatically saturated of from 1 to 6 carbon atoms or a heterofunctionality; e.g. halogen, particularly halogen of atomic number 9 to 35; or the two alphas may be taken together to form a divalent radical free of aromatic unsaturation of from 2 to 16 carbon atoms, more usually of from 2 to 10 carbon atoms wherein the annular carbons will normally be of from 1 to 4 carbon atoms, more usually of from 1 to 2 carbon atoms, or as already indicated, may be taken together with the two betas to form a tetravalent radical; the two betas are taken together to form a bond or a divalent radical free of aromatic unsaturation and of from 1 to 12 carbon atoms, more usually of from 1 to 6 carbon atoms, usually aliphatically saturated, wherein the annular carbons will normally be of from 1 to 4 carbon atoms, more usually from 1 to 2 carbon atoms; the divalent radical may have heterosubstituents, there being a total of 1 to 4 heteroatoms for the two betas and as already indicated, the two betas may be taken together with the two alphas to form a tetravalent radical; the two gammas may be hydrogen when they are situated at a bridge head, that is when the two alphas are taken together, hydrocarbon of from 1 to 12 carbon atoms, more usually of from 1 to 6 carbons atoms, and particularly from 1 to 3 carbon atoms, usually aliphatic of from 1 to 6 carbon atoms having from 0 to 1 site of ethylenic unsaturation and preferably saturated, substituted hydrocarbon or a heterofunctionality.

The substituents can vary widely normally being of from 1 to 3 heteroatoms, usually 1 to 2 heteroatoms and of from 0 to 6 carbon atoms, usually from 0 to 4 carbon atoms. The heteroatoms will usually be oxygen, nitrogen and halogen, particularly of atomic number 9 to 35. The functionalities include oxy(hydroxy and ether), non-oxo carbonyl (carboxylic acid, ester and amide), cyano, nitro, oxo-carbonyl, amino and halo, (fluoro, chloro and bromo), there generally being from 1 to 4 substituents, and other than halogen, generally from 1 to 2 substituents.

Illustrative compounds which find use in the subject invention include:

3,3,4,4-tetraethyldiazetine-1,2-dioxide;
3,4-dimethyl-3,4-diphenyldiazetine-1,2-dioxide;
3,4-dicyclopentyl-3,4-dimethyldiazetine-1,2-dioxide;
3,4-didodecyl-3,4-dimethyldiazetine-1,2-dioxide;
bicyclo[3,2,0]hept-2-en-2,3-diaza-2,3-dioxide;
bicyclo[4,2,2]dec-7-en-7,8-diaza-7,8-dioxide;
bicyclo[3,2,2]non-6-en-6,7-diaza-6,7-dioxide;
tricyclo[5,2,2,1$^{3,5}$]undec-8-en-8,9-diaza-8,9-dioxide;
tricyclo[6,2,2,0$^{2,7}$]dodec-9-en-9,10-diaza-9,10-dioxide;

The diazetine dioxides, because of their capability as quenching agents by virtue of their high singlet energies and low triplet energies, find a wide variety of applications. The compounds can be used in conjunction with substrates which undergo an undesired reaction as a result of being in a high energy state, usually caused by absorption of electromagnetic irradiation; e.g., light in the ultraviolet or visible region.

One such application is where a substrate absorbs light to go to an electronically activated state and then undergoes further reaction, either by itself or in combination with other molecules; e.g., oxygen, to form a product which does not have a desirable characteristic of the original product. A variation of the first situation is where the product of the reaction in itself is innocuous, but is subject to further reaction which results in undesirable modifications of the substrate. A third application is where the substrate is sensitive to oxygen in the singlet state, but not to the lower energy triplet state. Another application involves a substrate which, when activated, is capable of forming different products from the triplet state and the singlet state, so that by quenching the triplet state, the product from the singlet state becomes the predominant product. Pigments can serve to illustrate the situation where a substrate susceptible of excitation to an excited state can be protected by a diazadioxide. It is well known that pigments slowly degrade, changing or losing their color. Pigments which are chosen because of their light absorbing qualities, are subject to undergoing reactions, either uni- or bimolecularly to form products which either have different color characteristics than the original pigment or do not absorb light in the visible range. By quenching the excited triplet state of the pigment molecule, the reaction path passing through the triplet state is inhibited. In this manner, the lifetime of the pigment can be greatly extended.

The second situation is where an undesirable product is formed which may undergo further reactions of an undesirable nature. For example, a molecule is activated to an energy state where the molecule may react directly with oxygen to form a peroxide or hydroperoxide or react directly with a hydrogen donating material; e.g., an addition polymer, to introduce an unpaired electron in the polymer which is then able to react with oxygen to form a peroxy radical. The resulting peroxidic product can decompose to form additional radicals with further degradation of the molecule and/or polymeric material. By dissipating the energy of the excited state of the molecule by transfer of the energy to the stable quencher, this reaction sequence can be inhibited.

In many polymeric substrates the polymer may be relatively inert, but adventitious impurities or additives; e.g., dyes, may act as sensitizers or initiate reaction by abstraction of a hydrogen atom.

Those substrates which are sensitive to singlet oxygen, such as polyunsaturated compounds; e.g., fats, polymers, and the like, can be protected by the addition of the quencher. The quencher serves to dissipate the energy of most sensitizers which would otherwise transfer energy to oxygen. Inhibition of energy transfer to oxygen prevents formation of the oxygen singlet state and inhibits any reaction which requires the oxygen singlet state.

Finally, in many light catalyzed reactions, such as photocyclizations, isomeric products are formed, depending upon whether the product is formed from the triplet state or the singlet state. Therefore, by introducing the quencher into the reaction mixture, which efficiently quenches the triplet state, the desired singlet state product can be obtained.

The diazadioxide compounds are also found to be efficient free radical traps. Therefore, they find use in inhibiting chain reactions, such as oxidative polymer degradation, polymerization of free radical catalyzable monomers, oxidation of oxygen sensitive materials, such as ethers, polyenes, and the like, as well as for providing an induction period in a free radical catalyzed reaction.

Because of the great versatility of the diazadioxide, both as to particular application and to substrate, the amount of the diazadioxide which is employed will vary widely. Usually, at least about 0.01 weight percent based upon substrate will be employed and generally not more than 15 weight percent, more usually from about 0.05 weight percent to about 5 weight percent.

The diazadioxide compound can be combined with the substrate in a variety of ways. The compound can be dissolved in a common solvent with the substrate, can be extruded in combination with the substrate, mechanically mixed with the substrate, and the like. The amount of material which is employed will depend on the particular substrate, the conditions the substrate will be subjected to, compatability of the two materials, and the like.

Where the compound is used in solution as a triplet quencher, normally concentrations of the quencher will be less than about 0.1 M and may be as low as $10^{-6}$ M, depending on the particular compound and triplet state being quenched. In paints and pigments, the amount of the diazadioxide will generally vary from about 0.05 to 10 weight percent based on the weight of the dye. In polymers, to protect against oxidation, the amount of the diazadioxide will normally be at least 0.01 more usually at least about 0.1, and generally not exceeding about 2 weight percent based on the polymer.

The subject compounds are capable of quenching compounds having triplet states of energy greater than about 34 kcal/mole.

For those compounds which are activated by light radiation, the compounds will normally require light of energy not greater than that equivalent to a wavelength of 180 nm, usually of 210 nm. Either the substrate or a component of the substrate will have a sufficiently low lying excited state, so as to be readily activated by relatively mild energy sources; e.g., sunlight. The minimum amount of energy will be that equivalent to about 800 nm.

The substrate may not be one which chemically reacts with the diazadioxide to transfer the diazadioxide. For example, phosphates and phosphines react to reduce the diazadioxide.

The compounds which are employed in this invention will, for the most part, be cyclic, either mono- or polycyclic. Of particular interest are the novel azetine compounds which, for the most part, have the following formula:

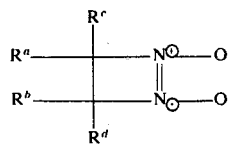

wherein: $R^a$, $R^b$, $R^c$, $R^d$ are of from 1 to 12 carbon atoms and 0 to 4 heteroatoms, and are hydrocarbon or substituted hydrocarbon, particularly aliphatic hydrocarbon of from 1 to 6 carbon atoms, or a heterofunctionality of from 1 to 3 heteroatoms.

The four-membered ring compounds of this invention are readily prepared from the 1,2-bis(dihydroxylamino) ethane or substituted ethane. These compounds have, for the most part, the following formula: (C)

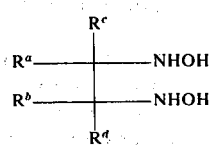

wherein:
$R^{a-d}$ have been defined previously.

In order to prepare the diazadioxide from the vicinal bis(dihydroxylamino) compound, the dihydroxylamino compound is oxidized with a mild oxidant, such as bromine water, sodium periodate, lead dioxide, manganese dioxide, and the like.

The oxidation of vicinal bis(dihydroxylamino) compounds is one route to the desired diazadioxide compounds. The bis(dihydroxylamino) compounds need not be vicinal, where a polycyclic structure maintains the two hydroxylamino groups in appropriate juxtaposition so as to permit the formation of the double bond between the two nitrogen atoms. However, for the most part, the bis(dihydroxylamino) compounds will be employed where vicinal, and will provide a compound having a four membered ring, with the two nitrogen atoms as annular atoms.

An alternative route to compounds which find use in this invention, has been previously reported, see references cited supra, and involves the addition of an azo group to a diene. Normally, a conjugated diene will be employed, although 1,4 dienes may be employed, which are restricted in their spatial relationship to permit a diaza bridge to be formed, as well as a new carbon-carbon bond between the other two carbon atoms involved in the double bonds. With the exception of 1,3,alkadienes, which provide monocyclic compounds, monocyclic and polycyclic conjugated dienes will provide polycyclic compounds of at least one order higher in the number of rings.

The compounds which are formed from the addition of an azo di(non-oxo-carbonyl) will involve a six-membered ring and, for the most part, come within the following formula:

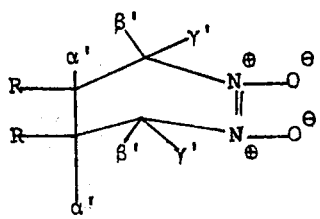

wherein:
the two (alpha')s may be the same or different and are hydrogen, hydrocarbon of from one to eight carbon atoms, more usually saturated aliphatic hydrocarbon of from one to three carbon atoms, substituted hydrocarbon of from one to eight carbon atoms or a heterofunctionality, where the substituent on the hydrocarbon group or the heterofunctionality can be halogen of atomic number 9-35, non-oxo-carbonyl, oxo-carbonyl, cyano, nitro, oxy, or the like, with the exception of halogen, there being normally not more than two substituents, more usually not more than one substituent; or may be taken together to form a divalent radical of from one to six carbon atoms, more usually of from one to two carbon atoms; or may be taken together with the two (beta')s to form a tetravalent radical of from two to twelve carbon atoms, more usually of from two to eight carbon atoms, which may be substituted or unsubstituted (hydrocarbon), the substituents having been previously indicated;

The two (beta')s may be the same or different and are hydrocarbon of from one to twelve carbon atoms, more usually saturated aliphatic hydrocarbon of from one to six carbon or substituted hydrocarbon of from one to twelve, usually one to six carbon atoms having from one to four substituents, with the exception of halogen, usually having from one to two substituents, the substituents having been indicated previously; or may be taken together to form a divalent radical of from one to eight carbon atoms, more usually of from one to six carbon atoms, only from one to two of the carbon atoms being annular; or, as previously indicated, may be taken together with the two (alpha')s to form a tetravalent radical;

the two (gamma')s may be the same or different and may be hydrogen, when the (beta')s are taken together, hydrocarbon of from one to twelve carbon atoms, more usually aliphatic hydrocarbon of from one to six carbon atoms having from 0 to 1 site of ethylenic unsaturation, and particularly saturated, or a heterofunctionality, the heterofunctionalities having been indicated previously; and, the two Rs are hydrogen, hydrocarbon of from 1 to 6 carbon atoms, usually saturated aliphatic or halogen of atomic number 9 to 35.

The third manner of preparation of these compounds is to have a diketone, where the ketonic groups are so spatially situated as to be held in juxtaposition, where a double bond can be formed between the two nitrogens of a dioxime prepared from the diketone. These compounds will normally be cyclic compounds where the ketone groups and the derivative dioximes are held in the appropriate spatial configuration by the rigidity of the ring structure to which they are attached.

The addition of the azo di(non-oxocarbonyl) is carried out under mild condition with such compounds as ethyl azodicarboxylate or N-phenylazodicarboximide The diene and azo compound are combined in a suitable solvent at mild temperatures, frequently below ambient, and the reaction allowed to proceed. Where the product has residual unsaturation, the unsaturation may be reduced by an convenient means. The non-oxocarbonyl groups may be removed by appropriate hydrolysis and the resulting hydrazo group oxidized to the desired diazadioxide.

Experimental

The following examples are offered by way of illustration and not by way of limitation, (All temperatures not so indicated are in centigrade).

EXAMPLE A

A. A mixture of 6 N NaOH (675 ml) and 356 g of 2-nitropropane (4 moles) was stirred and cooled while 320 g of bromine (2 moles) was added dropwise. Then ethanol was added and the solution refluxed gently (3 hours) before being mixed with ice water (1.5 l). The crystalline product was washed thoroughly with 50% ethanol. Yield 280 g, m.p. 213°–215° (lit. 215°).

B. 2,3-Dimethyl-2,3-dinitrobutane (175 g, 1 mole) was stirred in suspension in a solution of ammonium chloride (100 g, 1.9 moles) in 50% aqueous ethanol (2.1.) and kept below 15° while zinc dust (400 g, 6.2 moles) was added during 3 hours. The reaction mixture was allowed to come to room temperature and stirred overnight. After filtration, the combined filtrate and washings were acidified to pH 2 (150 ml conc. HCl) and evaporated under reduced pressure to a viscous state. Anhydrous potassium carbonate (1 kg) was stirred in while cooling, and the resulting powder extracted continuously with chloroform (2.5 l). overnight. The chloroform extract was dried over anhydrous sodium carbonate and evaporated to a viscous oil. Petroleum ether was added to promote crystallization of the product (40 g) m.p. 162°–163° (lit. 157°–159°).

C. Preparation of the above dinitro compounds is reported by L. W. Seigle and H. B. Hass, J. Org. Chem. 5, 100 (1940). In this work, the authors report a method for the synthesis of a variety of dinitro compounds, including those in which $R^1$, $R^2$, $R^3$ and $R^4$ are alkyl groups, aryl groups and asymmetrical combinations such as the following:

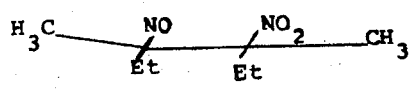 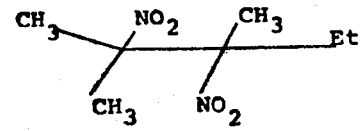

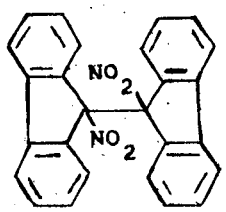 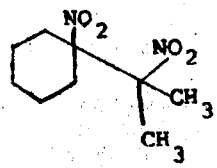

In those situations where a product is desired in which $R^1$ is the same as $R^3$ and $R^2$ is the same as $R^4$, a synthesis in accordance with Sayre: J. Am. Chem. Soc. 77, 6689 (1955) is preferably followed.

EXAMPLE I

3,3,4,4-Tetramethyl-1,2-diazetine-1,2-dioxide

A. To a stirred solution of N,N'-dihydroxy 2,3-dimethyl-2,3-diaminobutane (5 g) in water (250 ml), bromine (4 ml) was added dropwise at room temperature. The addition of bromine took 30 min. The reaction mixture was stirred for an additional period of 30 min. and the product extracted with chloroform. The organic extract was washed with 10% aqueous sodium sulfite to remove excess bromine, and then with a saturated solution of 10% sodium bicarbonate followed by water. The chloroform layer was dried with $MgSO_4$. Removal of the solvent in vacuo afforded white crystals of the product (2.9 g. 60%). Further recrystallization from methanol afforded colorless needles; m.p. 190°–2° (d); ir ($CHCl_3$) 1555, 1460, 1440, 1385, 1140, 1015, 910, and 625 $cm^{-1}$; nmr ($CDCL_3$) $\delta 1.64$ (s); UV ($CH_3CN$) 254 nm ($\epsilon 10,500$).

B. The product could also be obtained by oxidation of the dihydroxylamino precursor with sodium periodate. Thus, N,N-dihydroxy 2,3-dimethyl-2,3-diaminobutane (1.5 g) in water (50 ml) was stirred for 30 min. with aqueous sodium periodate (4.5 g in ca. 100 ml water). The product precipitated out and was washed with water, dried ($MgSO_4$), and evaporated to give the product (800 mg. 65°) T.L.C. (silica, $CHCl_3$/MeOH;4/1) one spot, $R_f 0.8$

EXAMPLE II

3,3,4,4-Tetramethyl-1,2-diazetine-1,2-dioxide

To a stirred aqueous solution of N,N'-dihydroxy 2,3-dimethyl-2,3-diaminobutane (6 g in 175 ml water) was added slowly (in ca. 1 ml aliquots) a saturated aqueous solution of sodium periodate (ca. 25 ml) until the reaction mixture turned brownish orange. Sodium periodate addition was stopped and excess periodate destroyed with aqueous sodium sulfite (10%). The product was extracted with chloroform, washed with saturated aqueous sodium chloride and dried. Removal of the solvent gave a mixture of products as a white solid. Vacuum (0.05 mm) sublimination at room temperature gave pale yellow microcrystals of an undesired compound (2) (1.3 g).

The residue was found to be pure compound (1) (nmr) and tlc analysis) (1.2 g). The relative ratio of (1) and (2), as determined by nmr of the crude mixture was 35:65 respectively.

EXAMPLE III

Tetracyclo [3,3,1,0$^{7,9}$, 0$^{6,8}$]-3,4-diaza-nona-3-en-3,4-dioxide

A. Into a reaction flask was introduced 20 g (0.115 mole) of ethyl azodicarboxylate, 18 g (0.16 mole) of norbornadiene and 100 mg of hydroquinone and heated at 150°–160° for 12 hours with the flask sealed. The resulting dark brown viscous liquid was dissolved in ether, which was then washed in succession with a saturated aqueous solution of sodium sulfite, 5% aqueous sodium bicarbonate and water. After drying the ether extract, the solvent was evaporated in vacuo. The residue was distilled at 0.1 mm Hg and a fraction collected at 135°–140°.

After some trial and error in chromatographing the product, neutral alumina (activity III) was employed and the product eluted with a 3:1 volume ratio of benzene and diethyl ether. The desired product was found in the later fractions.

B. The diester product obtained was hydrolyzed in accordance with the procedure described by Moriarty, J. Chem. Soc. 28, 2385 (1963). To a solution of 0.5 g (1.9 mmole) of the above product in 10 ml of methanol under nitrogen was added potassium hydroxide pellets (1 g, 0.018 mole). After refluxing under nitrogen for five hours, water was added (ca. 5 ml) to dissolve the potassium carbonate which had formed, resulting in a homogeneous solution. The mixture was then refluxed for an additional five hours, the solution cooled, and 2 ml of 30% hydrogen peroxide added, followed by refluxing the reaction mixture for 3 hours. A test of the reaction mixture with starch iodide showed the absence of peroxide. The mixture was then diluted with water and the product extracted with chloroform. The chloroform extract was then washed in succession with aqueous 10% sodium sulfite and water, followed by drying the chloroform layer with $MgSO_4$. The solvent was removed in vacuo. The residue was distilled at 5 mm Hg at 60°, to yield a thick, colorless liquid. On triturating the oil, a crystalline product was formed.

C. In a reaction flask was combined 3 ml of methylene dichloride, 1.5 ml (1.8 g) of trifluoroacetic anhydride and the mixture cooled in an ice bath. When the temperature reached 0°, 270 $\mu$ of 90% hydrogen peroxide was added and the mixture stirred for approximately 10–15 minutes until homogeneous. To the mixture was then added approximately 120 mg of the above product in 0.3 ml of methylene dichloride. After stirring for 2–3 hours, while cooled in an ice bath, the mixture was stirred in an ice bath for 24 hours. Any residual peracid was destroyed with saturated aqueous sodium sulfite solution. The reaction mixture was then neutralized with saturated aqueous sodium bicarbonate, followed by saturation with sodium chloride. The aqueous solution was then extracted with chloroform, the chloroform extract washed with saturated sodium chloride solution, followed by drying with magnesium sulfate. The solvent was then removed in vacuo, leaving a white crystalline residue. The product was then recrystallized from benzene and after two recrystallizations, gave needles, m.p. 184°–85°.

Anal. Calcd. for $C_7H_8N_2O_2$: C, 55.25; H, 5.30; N, 18.41; Found: C, 55.28; H, 5.30; N, 18.32.

EXAMPLE IV

Bicyclo[2,2,2]-2,3-diazaoct-2-en-2,3-dioxide

A. Following the procedure of Starnes, Jr., et al, J. Org. Chem. 32, 330 (1967), into a reaction flask fitted with a dropping funnel and a thermometer was added 17.7 g (0.1 mole) of 4-phenylurazole (prepared according to the procedure of Cookson, et al, Org. Synthesis 51, 121) and 500 ml of methylene dichloride. To the stirred mixture cooled in an ice bath was added 8.8 g 0.11 mole) of cyclohexadiene-1,3 and the temperature maintained at about 5°. A cold solution of 60 g of lead tetraacetate in 500 ml of methylene dichloride was added dropwise while stirring, followed by allowing the mixture to stir at room temperature overnight. The solid was removed by lowering the pressure until a final pressure of 0.1 mm Hg was achieved which was maintained for 1 hour. The resulting residue was successively washed with 300 ml of water, followed by filtration, 0.1 N nitric acid (300 ml) and 0.1 N sodium hydroxide (300 ml) and filtered. The residue was then washed with water and dried in air.

The brown residue was dissolved in about 1,500 ml of methanol and refluxed with Norite A for about 15 minutes, the solution filtered and then concentrated to about 300 ml. On cooling, white crystals precipitated to yield 13.1 g. m.p. 170°–171° (lit. 172°–174°).

B. The above product (2.55 g, 0.01 mole) in 75 ml of ethyl acetate was reduced with hydrogen over 10% Pd/C (150 mg) which had been prereduced for 15 minutes in 25 ml of ethyl acetate. After filtering the solution through Celite, the solvent was removed by evaporation to yield 2.6 g of white crystals, m.p. 211°–213°. The product could be recrystallized from methanol to give an analytical sample.

C. The above product (2.2 g) in a 1:1 mixture of ethylene glycol and water was introduced into a flask which was flushed with nitrogen for about 15 minutes, and maintained under a mild pressure of nitrogen. To the mixture was added 3.3 g of potassium pellets and the mixture refluxed for five hours. After cooling to room temperature, 20 ml of 30% hydrogen peroxide was added carefully, stirred for 2 hours, the contents then heated under reflux for 5 hours and cooled, there being no hydrogen peroxide remaining as evidenced by starch iodide paper. After removing aniline by steam distillation, the reaction mixture was diluted with water end extracted with chloroform. The chloroform extract was dried with MgSO$_4$ and the chloroform evaporated, leaving 600 mg residue. The product could be recrystallized from n-hexane to yield a product having a m.p. 144°–45°. (Cohen, J. Am. Chem. Soc., 84, 586, (1962).

D. The above product, 2,3-diazabicyclo[2,2,2]-2-octene (200 mg) in methylene dichloride was oxidized as follows. Into a flask was introduced 3 ml of methylene dichloride and 1.5 ml of trifluoroacetic anhydride and cooled in an ice bath. To the stirred mixture at 0° was added 270 μl of 95% hydrogen peroxide followed by the addition of 200 mg of the diazo compound in 3 ml of methylene dichloride. The mixture was then stirred overnight at room temperature. Excess peracid was destroyed by adding saturated aqueous sodium sulfite to the mixture cooled in an ice bath, followed by the careful addition of solid sodium bicarbonate until approximately a neutral pH was achieved. The sodium trifluoroacetate was filtered off, the organic layer separated and the aqueous layer extracted with chloroform. After combining the organic layers, the combined organic layers were washed with a satruated solution of aqueous sodium chloride, dried, and evaporated to yield 150 mg of a white solid. The product was dissolved in chloroform, refluxed with Norite A, the mixture filtered and the solvent removed. Recrystallization from chloroform/hexane, followed by benzene/chloroform yielded white crystals. m.p. 221°–222° (dec).

EXAMPLE V

Bicyclo[2,2,1]-2,3-diazahept-2-en-2,3-dioxide

A. 2,3-Dicarbethoxy-2,3-diazabicyclo[2,2,1]heptane was prepared according to the method of Gassman, et al, Org. Synthesis, 49, 1. Into a reaction flask was introduced 80 ml of ethylene glycol and nitrogen bubbled through for 0.5 hour. To the glycol was then added potassium hydroxide pellets (17 g) under nitrogen with stirring, followed by the rapid addition of 13.5 g of the diester indicated above, while the temperature was maintained between 125°–30°. After the addition, the temperature was maintained for another 1.5 hour, followed by the addition of 100 ml of water. The reaction mixture was cooled to room temperature while 100 ml of 30% hydrogen peroxide was added dropwise, followed by refluxing the mixture for four hours. After cooling and extracting the aqueous reaction mixture with 500 ml of chloroform, the organic extract was washed with aqueous sodium sulfite and then water, dried over MgSO$_4$ and the chloroform removed in vacuo, leaving 5.5 g.

B. The above product was oxidized as previously described. Pertrifluoracetic acid was prepared by combining 46.2 g of trifluoracetic anhydride (0.22 mole) and 5.4 ml of 90% aqueous hydrogen peroxide in methylene dichloride. The diazabicyclooctane in chloroform was added dropwise at 0°, the mixture stirred in an ice bath for about 3 hours, followed by stirring at room temperature for 3 days. Residual pertrifluoroacetate was destroyed with aqueous saturated sodium sulfite, followed by the additon of saturated aqueous sodium bicarbonate to the ice cooled solution with stirring until a pH of about 8 was obtained. The solution was then saturated with sodium chloride and extracted with chloroform continuously for a period of 48 hours. After drying the chloroform and evaporating the solvent, white crystals were obtained which were recrystallized twice from chloroform hexane and dried at room temperature over phosphorus pentoxide at 0.1 mm for 5 hours. m.p. 153°–154° (dec).

EXAMPLE VI

Hexacyclo[8,2,1,0$^{2,9}$,O$^{3,8}$,0$^{7,11}$,0$^{4,12}$]dodec-4,7-dichloro-5-en5,6-diaza-5,6-dioxide

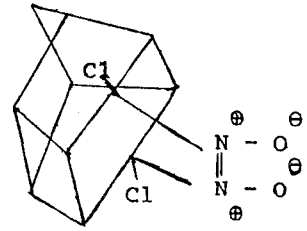

Into a reaction flask was introduced a cage diketone, pentacyclo[5,3,1,0$^{2,8}$,0$^{4,10}$,0$^{6,10}$]undeca-3,9-dione(1 g), 1.5 g of hydroxylamine hydrochloride in 30 ml of ethanol and 10 ml of pyridine and the mixture heated under reflux for four hours. By this time, most of the dioxime had crystallized out. The reaction mixture was stripped of substantially all solvent in vacuo, followed by dilution with a large excess of water. The dioxime was filtered off, washed with water and dried. Yield, 1 g (87%); m.p. 302°–304° (d). Recrystallization from dimethyl formamide and chloroform did not change the melting point.

B. The product (1 g) prepared above was suspended in 100 ml of dry diethyl ether and while cooled in a dry ice-acetone bath in the dark, chlorine gas was bubbled through the mixuture was stirring for 5 minutes until a yellow color persisted. The reaction mixture was then stirred for an additional 30 minutes, followed by allowing it to warm to room temperature and stirring for another 1.5 hours. The resulting precipitate was filtered and washed thoroughly with ice cold 10% aqueous sodium hydroxide, followed by water and then methanol. The sample was dried at 80° Yield, 1 g (75%), recrystallization from methanol gave a product as white needles, m.p. 233°–4°.

EXAMPLE VII

Bicyclo[2,2,2]hex-1,4-dichloro-2,3-diaza-2-en-2,3-dioxide.

A. An aqueous solution of 5 g hydroxylamine hydrochloride and 6.2 g sodium carbonate in 30 ml water was combined with an aqueous solution of 2.24 g of 1,4-cyclohexadione in 10 ml water, and the mixture stirred for 10 min, when a white precipitate formed. After refluxing for 1 hour, followed by cooling, the dioxime was isolated 2.3 g, 81%, m.p. 196°–9°.

B. The dioxime (2 g) was suspended in 20 ml anhydrous diethyl ether and combined at room temperature with ~ 10 g nitrosyl chloride in ~ 25 ml ether. After 20 hours, the solution was filtered and the product obtained. 1.1 g, 33%. After dissolving in ethanol and decolorizing with Norit A, concentration of the ethanol solution yielded 0.75 g m.p. 160°–165° (dec).

EXAMPLE VIII

Bicyclo[2,2,2]hex-1,4-dichloro-2,3-diaza-2-en-2,3-dioxide

Cyclohexane-1,4-dioxime (4.0 g) suspended in 200 ml of anh. diethyl ether under anhydrous conditions was cooled in a dry ice bath (~−70°). Chlorine gas was then slowly bubbled through the stirring suspension until a green-yellow color persisted. Agitation was continued, followed by allowing the mixture to warm to ambient temperature and then stirring for an additional 30 min. The solid was filtered, washed with dry ether, aqueous saturated sodium carbonate, water and finally ethanol. After drying in an oven at 80°, 2.7 g (45%) was isolated.

EXAMPLE IX

Bicyclo[2,2,1]hept-2,3-diaza-2-en-2,3-dioxide

A. Ethylene glycol (150 ml) under anhydrous conditions was flushed with nitrogen and 17 g KOH added. When the KOH had dissolved, the solution was heated to 125° and 13.5 g, 2,3-dicarbethoxy-2,3-diazabicyclo[2,2,1]heptane quickly added dropwise with stirring to maintain the temperature at 125°–130°. The temperature was then maintained for an additional 1.5 hour, followed by dilution with 100 ml water. After cooling the reaction mixture, 100 ml of a 30% solution of hydrogen peroxide was carefully added dropwise. After 4 hours of stirring, the solution was extracted with chloroform and the extract washed with saturated aqueous sodium sulfite, followed by water. After drying, the solvent was removed in vacuo to leave a solid residue which was further dried with a slow stream of nitrogen. 5.5 g, 100%.

B. The above product (200 mg) in 20 ml chloroform was stirred with 1.4 g m chloroperbenzoic acid for 2 hours, followed by refluxing for about a day. After cooling, excess peracid was destroyed with aqueous sodium sulfite and the organic layer washed with 10% aqueous sodium bicarbonate and water. After drying the solution and removing the solvent, the semisolid residue was purified by preparative tlc (silica; $HCCl_3$/MeOH,9:1). The product weighed 180 mg and was easily sublimable m.p. 93°–95°.

C. A chloroform solution (100 mg in 1.5 ml) of the above product was stirred at 0° for 2 hours with trifluoroperacetic anhydride (1.5 ml); 3 ml methylene chloride 0.27 ml 90% hydrogen peroxide). After stirring the mixture overnight at room temperature, excess peracid was destroyed with saturated aqueous sodium sulfite and the acid neutralized carefully with saturated aqueous sodium bicarbonate. After saturating the aqueous solution with NaCl, the solution was extracted with chloroform and the chloroform dried. Removal of the solvent yielded the cyrstalline product. m.p. 150°–52°.

In order to demonstrate the versatility of the subject compounds, their activity as free radical inhibitors was demonstrated. The compound employed was the exemplary compound of Example V. Into one test tube (A) was introduced 150 mg (~2 wt. %) of benzoyl peroxide in freshly distilled styrene (7.5 ml) and into another test tube (B) was introduced 150 mg of benzoyl peroxide. 25 mg of the compound of Example V (0.33 weight percent) and 7.5 ml of styrene. Five ml of each of solutions A and B were introduced into different compartments of a petri dish divided into four equal parts. The dish was covered and heated at a temperature of about 80°–90°. While there was some loss of styrene by evaporation, within two hours, the material of test tube A was a hard solid mass, while the material of test tube B was still mobile and fluid, although it had formed a light yellowish cast.

The above experiment was repeated employing 2 ml aliquots of each of the solutions which were introduced into 5 ml volumetric flasks, which was covered with aluminum paper, and the samples heated in the manner described above. Again, within two hours, the sample without the diazadioxide was solid, while the other sample was a light yellowish fluid.

To demonstrate the effect with dyes, the dye alizarin, an anthraquinone dye, was employed. A dilute solution of alizarin in ethanol was prepared, filtered, and the filtrate divided into two equal aliquots. To one of the aliquots was added a small amount of the compound of Example V. The tubes were then stoppered with serum caps and nitrogen bubbled through the tubes for two minutes to remove oxygen.

The two tubes were then irradiated with a BH-6 lamp using a Corning 7380 filter to provide light of wavelength equal to or greater than 340nm. After irradiation for about 3 hours, the solution without the diazadioxide appeared muddy, while the solution with the diazadioxide was virtually unchanged. The solutions were then irradiated for an additional 24 hours which resulted in almost complete dissipation of the color in the solution without the diazadioxide, while the other sample remained substantially the same color.

To demonstrate the effectiveness of the subject diazadioxide compound as triplet quenchers, the following experiments were carried out.

Two aliquots of 1:1 solution of methanol and tert.-butanol were prepared having $5.7 \times 10^{-3}$ molar concentrations of ditoluoyl. In one of the solutions, the compound of Example I was introduced at a concentration of $5.41 \times 10^{-3}$ M. The two solutions were irradiated for about 57 minutes with UV light having a wavelength equal to or greater than about 390nm. While the sample without the compound of Example I underwent a significant change in spectrum having an isosbestic point at 375nm, there was substantially no change in the spectrum of tube having the compound of Example X.

Under analogous conditions, the compound of Example I was found to inhibit the addition of oxygen to anthracene, when anthracene was irradiated with light in the presence of oxygen, under conditions known, in the absence of quencher, to result in the addition of oxygen to anthracene.

Finally, the Ullman color test, described in Weissberger, Techniques of Organic Chemistry, Volume 14, Interscience Publishers, New York (1969) indicated that the triplet energy value was equal to or less than about 45 kcal for the compound of Example I. This value is extremely low as compared to most available quenchers.

In order to further determine the triplet energy of a number of compounds prepared in this invention, a kinetic study was carried out. An ethanolic solution was prepared of naphthalene and 2,5-diphenylisobenzofuran with and without a sample of the diazadioxide compound. The solutions were irradiated with light of 310nm in the presence of air, conditions which, in the absence of a quenching reagent, results in the rapid addition of oxygen to the isobenzofuran. The rate of the reaction is followed by the loss of absorption at 410nm.

By determining the rate of addition of oxygen to the isobenzofuran in the presence and absence of a triplet quencher at varying concentrations of the triplet quencher and plotting the raio of quantum yield in the presence and absence of a triplet quencher, a relatively accurate determination of the triplet energy of the quencher can be determined. By following this procedure, the triplet energy for the compound of Example I is estimated to be about 45 kcal. The triplet energy for the compound of Example III is about 38 kcal, Example IV, about 42 kcal, Example V about 37 kcal, Example VI about 35 kcal, and Example VII about 34 kcal. By way of comparison, eosin has a triplet energy of 43 kcal per mole, anthracene 42 kcal per mole and crystal violet 39 kcal per mole.

In accordance with the subject invention, highly efficient protection of substrates subject to free radical attack or photoinduced reactions is achieved. The diazadioxides are found to be extremely efficient free radical traps and oxidation inhibitors and can be used for the protection of pigments, polymers, addition-polymerizable monomers and the like, in a wide variety of environments, such as molded objects; extruded objects, e.g. films and fibers; liquids, e.g. solutions; colloidal solutions, e.g. paints; or physically admixed with a substrate.

In addition, the molecules can be used as quenchers for molecules in their electronically excited state. Because of the simple structure, low energy and solubility in a wide variety of solvents, the diazadioxides are particularly versatile. In addition, they are colorless and do not interfere with the spectrophotometric kinetic determinations at wavelengths in the visible range.

Although the foregoing invention has been described in some detail by way of illustration and example for purposes of clarity of understanding, it will be obvious that certain changes and modificatons may be practiced within the scope of the invention as limited only by the scope of the appended claims.

What is claimed is:

1. Compound of the formula:

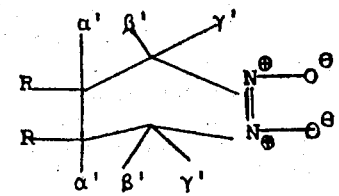

wherein:
 the two $\alpha$'s and the $\beta$'s are taken together to form a saturated unsubstituted aliphatic tetravalent group of from 2 to 12 carbon atoms;
 the two $\gamma$'s are the same or different and are saturated aliphatic hydrocarbon of from 1 to 6 carbon atoms, halogen of atomic number 9 to 35 or hydrogen; and
 the two R's are the same or different and are hydrogen, saturated aliphatic hydrocarbon of from 1 to 6 carbon atoms or halogen of atomic number 9 to 35.

2. Compound according to claim 1, wherein;
 the two $\alpha$'s and the two $\beta$'s form a 2,3,5,6-norbornane tetravalent hydrocarbon group.

3. Hexacyclo[8,2,1,0$^{2,9}$,0$^{3,8}$,0$^{7,11}$,0$^{4,12}$]-dodeca-4,7-dichloro-5-en-5,6-diaza-5,6-dioxide, of the formula:

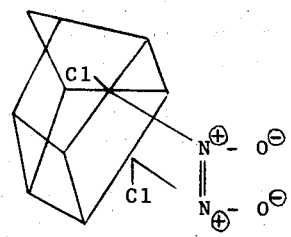

* * * * *